(12) United States Patent
Maldonado et al.

(10) Patent No.: US 10,463,767 B2
(45) Date of Patent: Nov. 5, 2019

(54) MOLDABLE BONE COMPOSITION

(71) Applicant: Vivex Biomedical Inc., Marietta, GA (US)

(72) Inventors: Edgar S. Maldonado, Miami, FL (US); Silvia Daniela Gonzales, Miami, FL (US); Wendy W. Weston, Miami, FL (US); Shabnam Namin, Miami, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 96 days.

(21) Appl. No.: 15/136,339

(22) Filed: Apr. 22, 2016

(65) Prior Publication Data

US 2017/0304053 A1    Oct. 26, 2017

(51) Int. Cl.
*A61F 2/28* (2006.01)
*A61L 27/36* (2006.01)
*A61L 27/50* (2006.01)

(52) U.S. Cl.
CPC .......... *A61L 27/50* (2013.01); *A61L 27/365* (2013.01); *A61L 27/3608* (2013.01); *A61L 27/3691* (2013.01); *A61F 2002/2817* (2013.01); *A61F 2002/2835* (2013.01); *A61F 2310/00359* (2013.01); *A61L 2430/02* (2013.01)

(58) Field of Classification Search
CPC ............... A61F 2002/2835; A61F 2/28; A61F 2210/0004; A61F 2002/2817; A61F 2002/30092; A61F 2002/30131; A61F 2002/30133; A61F 2002/30224; A61F 2002/3023; A61F 2002/30308; A61F 2002/30383; A61F 2002/30556; A61F 2210/0085

See application file for complete search history.

(56) References Cited

U.S. PATENT DOCUMENTS

| | | |
|---|---|---|
| 3,458,397 A | 7/1969 | Myers et al. |
| 4,172,128 A | 10/1979 | Thiele et al. |
| 4,440,750 A | 4/1984 | Glowacki et al. |
| 5,073,373 A | 12/1991 | Oleary et al. |
| 5,236,456 A | 8/1993 | Oleary et al. |
| 5,486,359 A | 1/1996 | Caplan et al. |
| 5,490,937 A | 2/1996 | vanReis |
| 5,531,791 A | 7/1996 | Wolfinbarger |
| 5,733,542 A | 3/1998 | Haynesworth et al. |

(Continued)

OTHER PUBLICATIONS

Chu Chang Chua, Deborah Ceiman, and Roger L. Ladda; "Transforming Growth Factors Released From Kirsten Sarcoma Virus Transformed Cells Do Not Compete for Epidermal Growth Factor Membrane Receptors"; Journal of Cellular Physiology 117:116-122 (1983).

(Continued)

*Primary Examiner* — Ann Schillinger
(74) *Attorney, Agent, or Firm* — David L. King

(57) ABSTRACT

A moldable bone composition consists of a mixture of: cortical bone and cancellous bone. The cortical bone is formed in three portions, a mineralized shaving portion and a demineralized shaving portion and a mineralized powder portion. The cancellous bone is formed in a mineralized crushed cancellous portion. The portions are free-dried and mixed together to form a freeze-dried moldable bone composition.

15 Claims, 9 Drawing Sheets

(56) References Cited

U.S. PATENT DOCUMENTS

| | | | |
|---|---|---|---|
| 6,432,436 | B1 | 8/2002 | Gertzman et al. |
| 6,437,018 | B1 | 8/2002 | Gertzman et al. |
| 6,458,375 | B1 | 10/2002 | Gertzman et al. |
| 6,576,249 | B1 | 6/2003 | Gendler et al. |
| RE38,522 | E | 5/2004 | Gertzman et al. |
| 6,911,212 | B2 | 6/2005 | Gertzman et al. |
| 6,998,135 | B1 | 2/2006 | Sunwoo et al. |
| 7,015,037 | B1 | 3/2006 | Furcht et al. |
| 7,019,192 | B2 | 3/2006 | Gertzman et al. |
| 7,045,141 | B2 | 5/2006 | Merboth et al. |
| 7,067,123 | B2 | 6/2006 | Gomes et al. |
| RE39,587 | E | 4/2007 | Gertzman et al. |
| 7,488,348 | B2 | 2/2009 | Truncale et al. |
| 7,659,118 | B2 | 2/2010 | Furcht et al. |
| 7,847,072 | B2 | 12/2010 | Thorne |
| 7,879,103 | B2 | 2/2011 | Gertzman et al. |
| RE42,208 | E | 3/2011 | Truncale et al. |
| 7,901,457 | B2 | 3/2011 | Truncale et al. |
| 8,075,881 | B2 | 12/2011 | Verfaillie et al. |
| RE43,258 | E | 3/2012 | Truncale et al. |
| 8,221,500 | B2 | 7/2012 | Truncale et al. |
| 8,292,968 | B2 | 10/2012 | Truncale et al. |
| 8,354,370 | B2 | 1/2013 | Kopen et al. |
| 8,394,419 | B2 | 3/2013 | Borden |
| 8,834,928 | B1 | 9/2014 | Truncale et al. |
| 9,138,508 | B2 | 9/2015 | Borden |
| 9,138,509 | B2 | 9/2015 | Sunwoo et al. |
| 9,192,695 | B2 | 11/2015 | Shi |
| 2001/0018614 | A1* | 8/2001 | Bianchi ............... A61F 2/28 623/16.11 |
| 2003/0039676 | A1* | 2/2003 | Boyce ............ A61B 17/0401 424/423 |
| 2003/0059414 | A1 | 3/2003 | Ho et al. |
| 2004/0058412 | A1 | 3/2004 | Ho et al. |
| 2005/0181502 | A1 | 8/2005 | Furcht et al. |
| 2006/0004189 | A1 | 1/2006 | Gandy |
| 2007/0049739 | A1 | 3/2007 | Troxel |
| 2007/0224177 | A1 | 9/2007 | Ho et al. |
| 2013/0195810 | A1 | 8/2013 | Crawford et al. |
| 2014/0005793 | A1 | 1/2014 | Koford et al. |
| 2014/0030235 | A1 | 1/2014 | Varney et al. |
| 2015/0012107 | A1 | 1/2015 | Koford et al. |
| 2016/0030639 | A1 | 2/2016 | Shi |
| 2016/0135954 | A1* | 5/2016 | Schlachter .......... A61F 2/28 623/23.63 |

OTHER PUBLICATIONS

Yawei Liua, Anders Kalenb, Olof Ristob & ; "Time- and pH-dependent release of PDGF and TGF-β from platelets <emph type="2">in vitro</emph>"; pp. 233-237 Platelets vol. 14, Issue 4, 2003 ; Published online: Jul. 7, 2009.

Trinity Elite, product, sales brochure, TT-1515, Orthofix Holdings Inc, Oct. 2015.

Osteocel bone graft web page, http://www.nuvasive.com/patient-solutions/nuvasive-integrated-surgical-solutions/osteocel-bone-graft/; 2016.

* cited by examiner

MOLDABLE BONE COMPOSITION

TECHNICAL FIELD

This invention is a moldable mineralized and demineralized bone composition. More specifically, a composition that can be formed into a molded shape retaining structure by adding appropriate compatible fluid for bone repair and a method of manufacture and use of said composition.

BACKGROUND OF THE INVENTION

The manufacture and use of bone allografts from bone tissue is well known. The use of particles of various specific sizes and distributions have been determined to have beneficial characteristics for new bone growth in the treatment of osseous defects and bone voids.

The issue of getting the repair composition to stay in position has been addressed for various formulations made into malleable paste or putty by the addition of collagen or other gelatinous materials.

The present invention provides an improvement over those prior art materials.

SUMMARY OF THE INVENTION

A moldable bone composition consists of a mixture of: cortical bone and cancellous bone. The cortical bone is formed in three portions, a mineralized shaving portion and a demineralized shaving portion and a mineralized powder portion. The cancellous bone is formed in a mineralized crushed cancellous portion. The portions are free-dried and mixed together to form a freeze-dried moldable bone composition. When subjected to a fluid, the composition can be molded to a desired shape. The crushed cancellous bone is made from freeze-dried morselized cancellous ground to a size of 1000 to 1700 microns. The cortical bone powder is ground to 300 microns or less. The cortical shavings are long thin strips cut from cortical bone plates having a length of greater than 5 cm. The cortical shavings are strands having a length greater than 3 mm. The mixture has a percentage of demineralized cortical bone shaving portion either by weight or volume in the range of 15 to 25%; a percentage of mineralized dry cortical bone shaving either by weight or volume in the range of 70 to 50%; a percentage of mineralized dry cortical bone powder either by weight or volume in the range of 5 to 15% and a percentage of dry crushed cancellous either by weight or volume in the range of 5 to 15%.

The preferred moldable bone composition has a percentage of 20% demineralized cortical bone shaving, 60% dry mineralized cortical bone shaving, 10% dry cortical bone powder and 10% dry crushed cancellous. The composition is formed as a freeze-dried material packaged in jars wherein the packaged mixture is stored at room temperature or frozen.

A method of manufacturing a moldable bone composition has the steps of: cutting cortical bone plates into long pieces; shaving the cortical bone plates to form cortical strands or shavings 3 mm or greater in length; demineralizing a first portion of the cortical shavings; grinding another portion of the cortical shavings; resulting the cortical bone having three portions, a demineralized cortical shavings portion, a mineralized cortical shavings portion and a powered cortical portion; cutting and grinding cancellous bone to form a portion of mineralized crushed cancellous bone from a size of 1000 to 1700 microns; freeze-drying each portion; and mixing together all of the portions in a predetermined ratio to form a freeze-dried composition.

Definitions

DBM—Demineralized Bone Matrix.

Cryopreserved—Tissue frozen with the addition of, or in a solution containing, a cryoprotectant agent.

Freeze Dried/Lyophilized—Tissue dehydrated for storage by conversion of the water content of frozen tissue to a gaseous state under vacuum that extracts moisture.

Malleability is the ability of DBM aseptic paste to be molded into different shapes with no visible cracks.

Normal Saline—0.9% Sodium Chloride Solution.

PBS—Phosphate Buffered Saline.

SRI—an equipment sterilization service company.

BRIEF DESCRIPTION OF THE DRAWINGS

The invention will be described by way of example and with reference to the accompanying drawings in which.

DETAILED DESCRIPTION OF THE INVENTION

The present invention encompasses the manufacturing of an aseptic moldable bone composition derived from human cadaveric cortical and cancellous bone. Cortical and cancellous bone is obtained from male or female donors. Full body donors with no joint replacements are preferred. The donors' medical and social history are screened for medical conditions such as osteoporosis and alcohol abuse, which may hinder the intended purpose of the final product. The demineralization process of bone tissue exposes morphogenetic proteins and other intrinsic growth factors involved in providing the osteoinductive signal to form new bone. Therefore, the application of moldable bone composition aseptic products is intended to aid in the treatment of osseous defects and bone voids. The moldable bone composition is ready for implantation and may or may not require thawing. At room temperature with appropriate fluid added, moldable bone composition is moldable.

Figure 1:
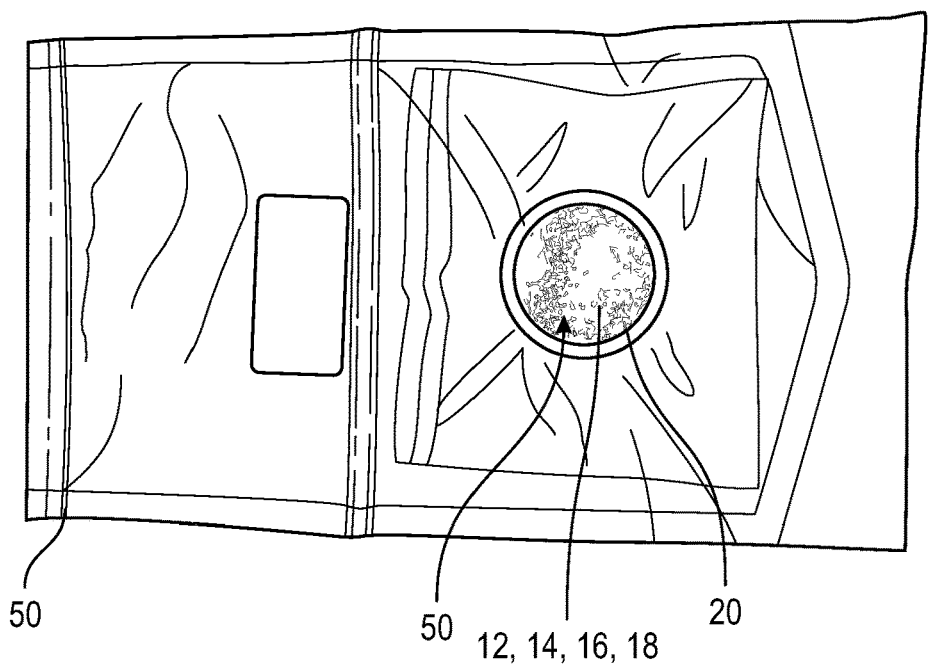
FIG. 1 shows a photograph of the moldable bone composition in a container packaged in a clear sealed bag.
Figure 2:
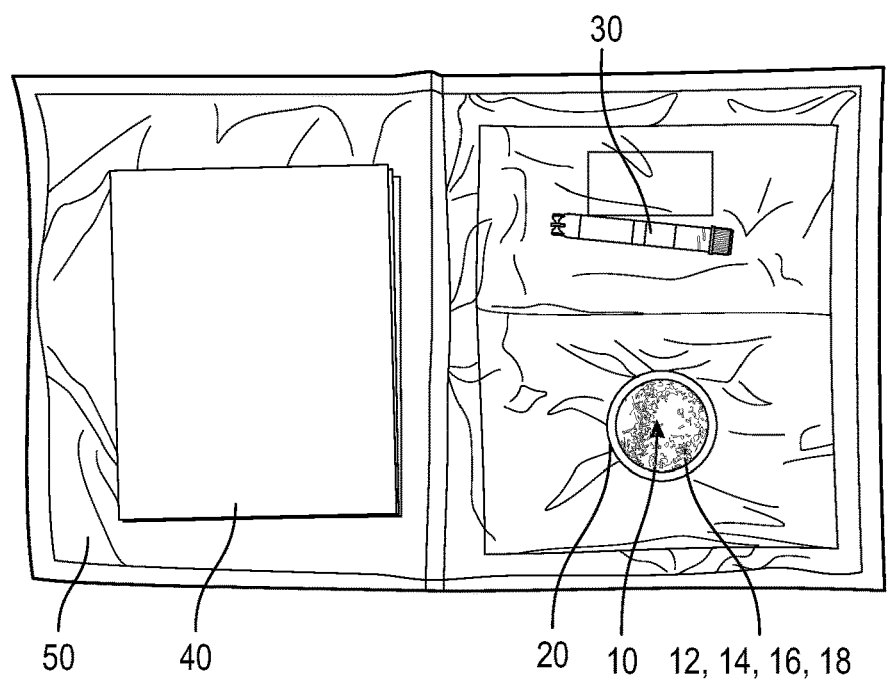
FIG. 2 is a photograph of the moldable bone composition in a container packaged in a clear sealed bag with a vial of cells suspended in a liquid.

The moldable bone composition 10 is entirely derived from aseptic allograft cortical and cancellous bone. The cortical bone is aseptically cleaned, cut and shaved in order to obtain cortical bone shavings. Part of the cortical bone shavings are demineralized. The cancellous bone is cleaned, cut and crushed. Moldable bone composition is prepared by mixing mineralized shavings and powder, demineralized cortical shavings and crushed cancellous bone. As shown in FIG. 1, the moldable bone composition 10 products of 2.5, 5 or 10 cc are distributed into containers, packaged in final packaging, as shown in FIG. 1 or 2 is illustrated in FIG. 7, and stored at room temperature or frozen until distribution to the end user.

Figure 7:
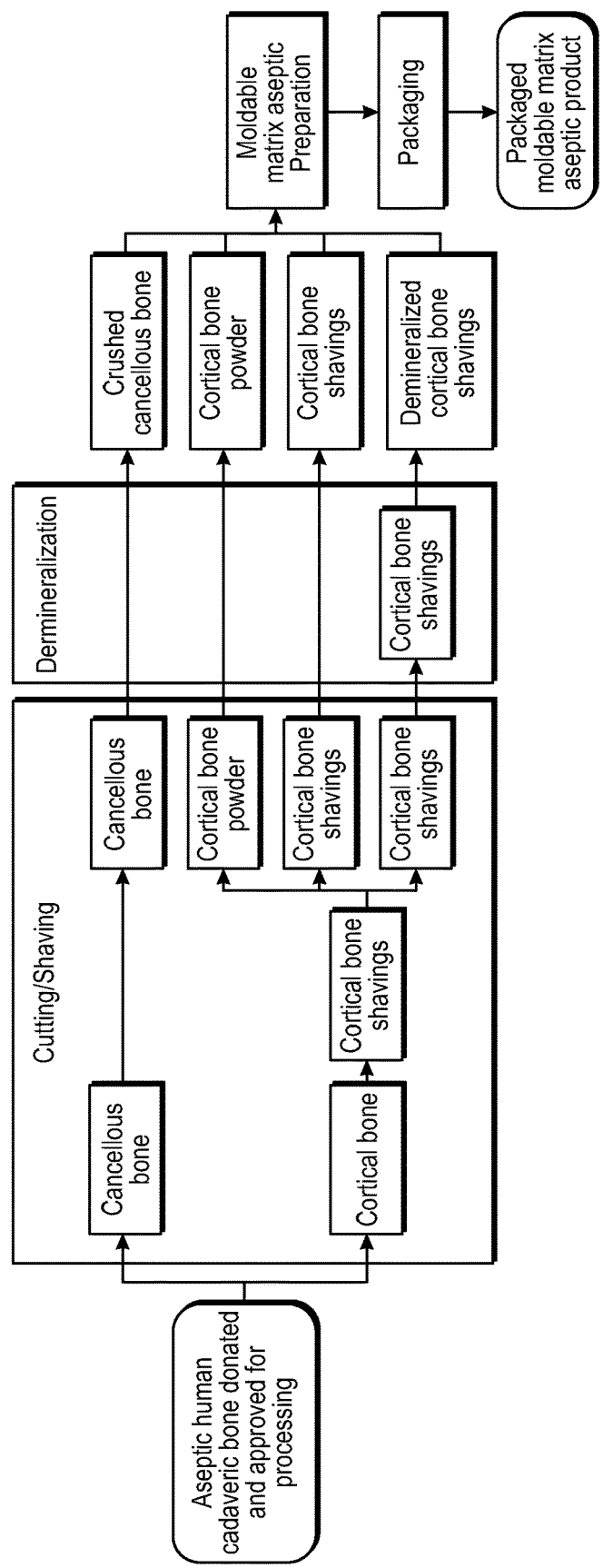
FIG. 7 is a schematic illustration of the moldable bone composition manufacturing process outline.

The overall manufacturing process outline for the moldable bone composition product is shown in FIG. 7. The input of the process is the donated and approved for processing aseptic human cadaveric cortical and cancellous bone immediately frozen after recovery. Once the cortical and cancellous bone has been processed, the output is the packaged moldable bone composition product. The moldable bone composition process itself has been divided into six subprocesses with their own respective inputs and outputs. The breakdowns of these individual subprocesses are described, as shown in FIGS. 8-16.

Figure 8:
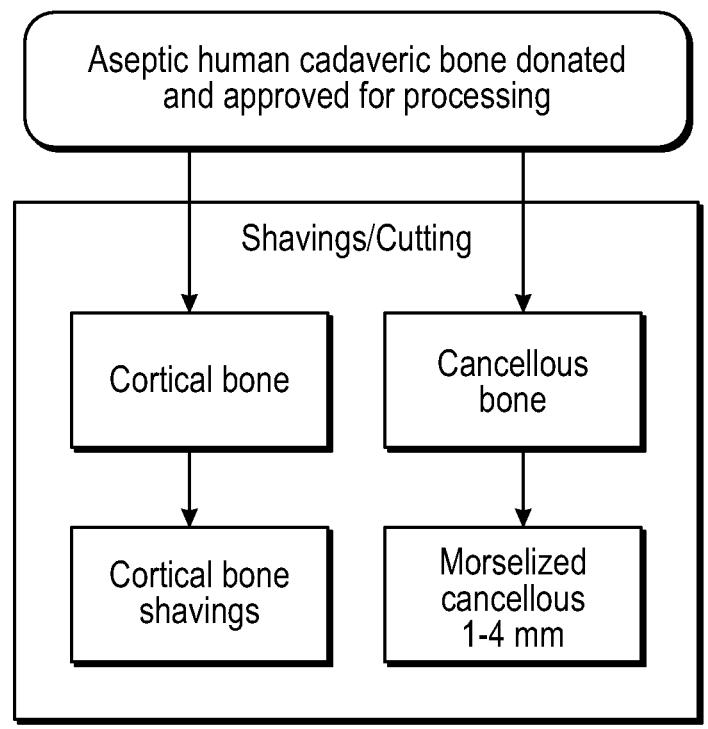
FIG. 8 shows the subprocess of shaving/cutting taken from FIG. 7.

The Shaving/Cutting subprocess is illustrated schematically in FIG. 8.

Prior to cutting the donated and approved for processing aseptic human cadaveric cortical and cancellous bone, all extraneous material such as muscle fibers, adipose tissue, and periosteum are removed from the tissue. Bones are then rinsed a minimum of 3 times with physiological grade normal saline (0.9% Sodium Chloride). Using a band saw, the bones are cut in a manner that the cortical and cancellous portions are separated. Cortical bone shafts are cut in half longitudinally and placed in basins with normal saline. Cancellous bone cut into pieces and crushed. Further cleaning and cutting of cortical and cancellous bone is as detailed below.

Cortical Bone Shavings:

Cortical bone plates are cut into approximately 6.5 cm long pieces. The bone plates are placed in a wash can with normal saline. The wash can is wrapped and agitated for 5 to 10 minutes to remove any blood and adipose tissue. Bone tissues are then rinsed with normal saline as often as needed to clean tissue of blood and/or fatty deposits. The bone tissues are shaved using a shaving machine set to produce >3 mm strands. Cortical bone shavings are collected in a basin and rinsed with hydrogen peroxide if required for no more than 10 minutes to remove fat/blood if necessary. Cortical bone shavings are rinsed a minimum of three times with sterile water to remove any residual hydrogen peroxide. The shavings are stored at −80° C. as schematically detailed at the top of FIG. 5.

Cancellous Bone:

Cancellous bone is cut into small pieces using a band saw. The small pieces are rinsed a minimum of three times in normal saline and then placed into a metal container with normal saline. The container is wrapped, placed on a shaker and mechanically agitated for 5 to 10 minutes. The bone tissue is then crushed into approximately 1-4 mm pieces using a morselizer. The tissue is rinsed a minimum of three times with normal saline in order to remove any remnants of blood and/or fat deposits. The bone pieces are rinsed with hydrogen peroxide if required for no more than 10 minutes to remove fat/blood. The bone pieces are rinsed a minimum of three times with sterile water to remove any residual hydrogen peroxide. The cancellous bone tissue is placed in a metal cube and stored at −80° C. prior to freeze-drying.

Figure 9:
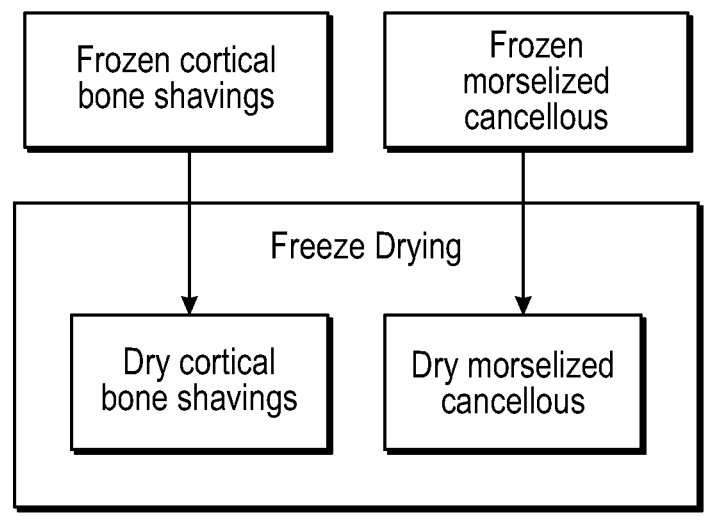
FIG. 9 shows the subprocess of freeze-drying taken from FIG. 7.
Figure 14:
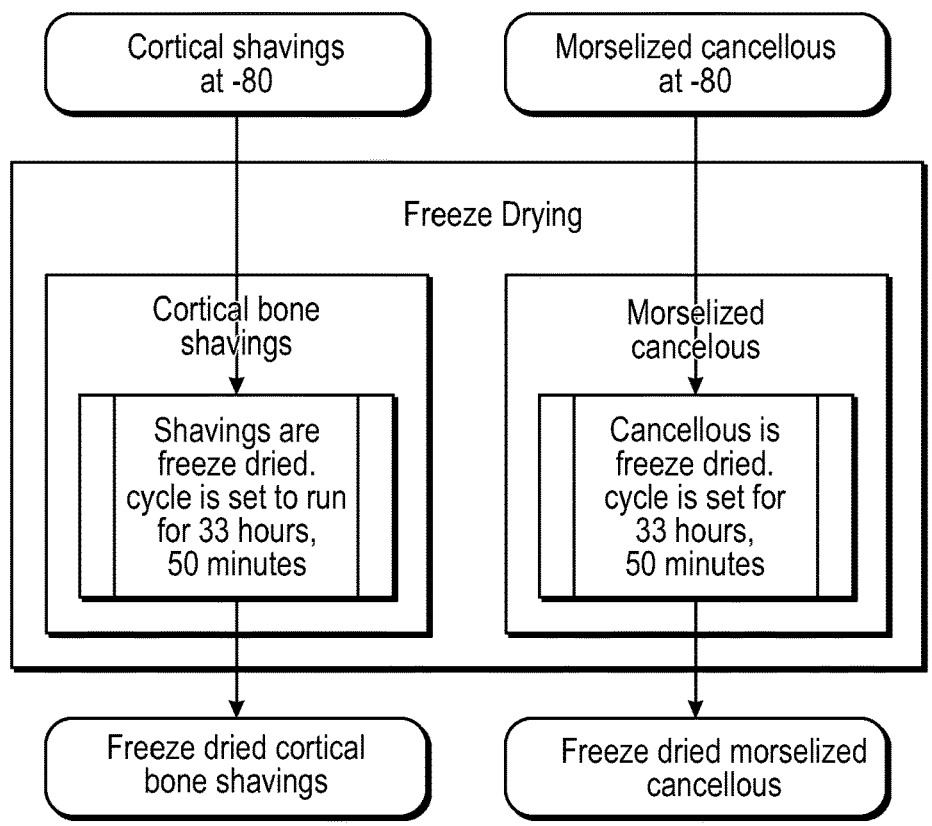
FIG. 14 shows the subprocess of freeze-drying taken from FIG. 7.

The first Freeze-Drying subprocess is shown in FIGS. 9 and 14.

Once the cortical bone shavings and morselized cancellous have been created and separately stored at −80° C., the frozen material is then prepared to undergo the freeze drying process. The shavings and cancellous are placed in metal cubes on sterile drying trays. The drying trays are then placed inside of a freeze dryer which is set to run for 33 hours 50 minutes. This cycle has shown to sufficiently dry the tissue without affecting the structural and chemical properties of the tissue. It is understood the timing can vary based on the equipment and procedures used and the above is exemplary of the preferred process for the inventors' equipment. By sufficiently drying, the inventors intend the moisture content to be less than 10 percent, preferably about 5 percent.

Figure 10:
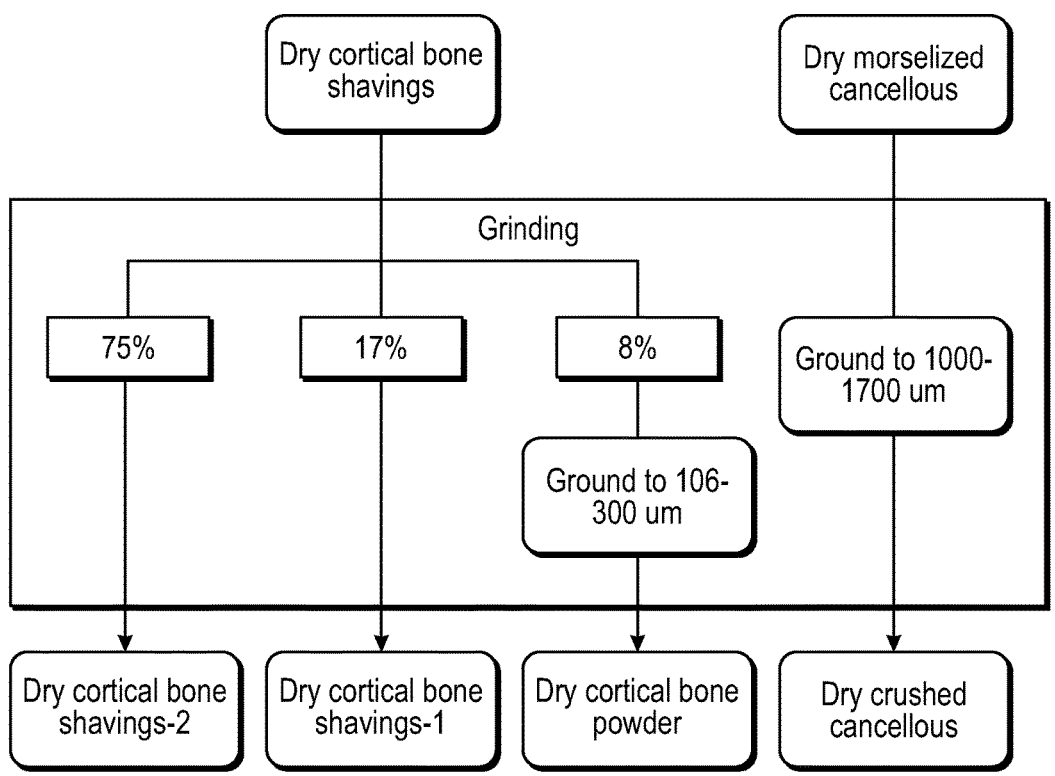
FIG. 10 shows the subprocess of grinding taken from FIG. 7.
Figure 15:
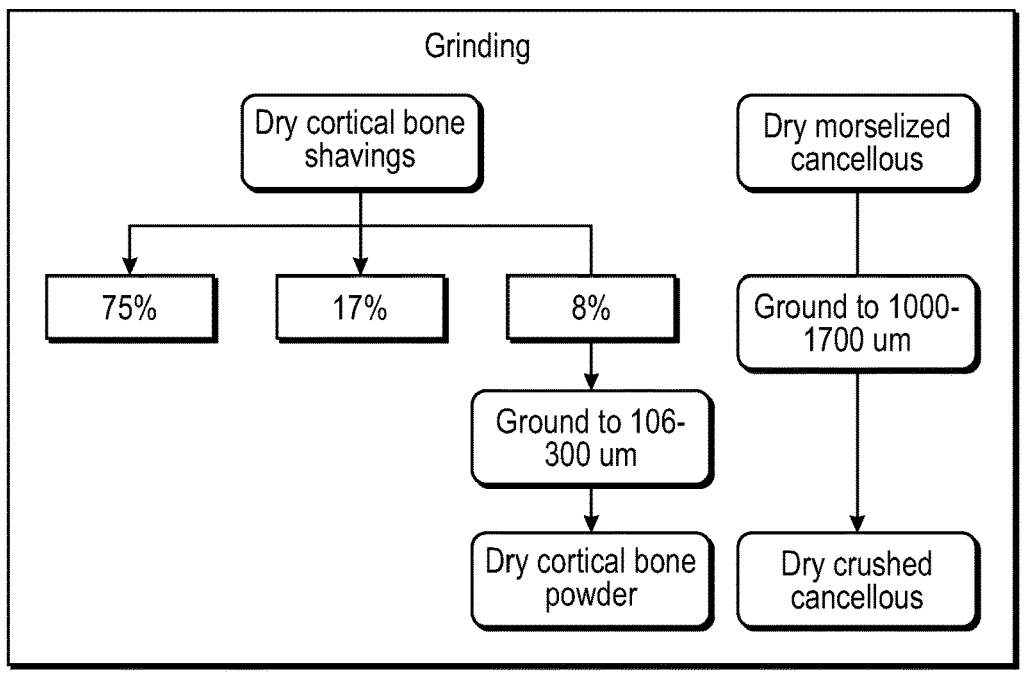
FIG. 15 shows the subprocess of grinding taken from FIG. 7.
Figure 16:
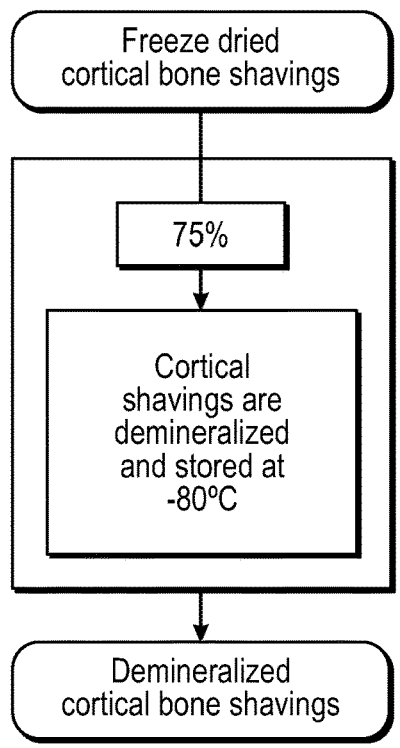
FIG. 16 shows the subprocess of demineralizing cortical bone shavings.

The Grinding subprocess is shown in FIGS. 10 and 15. The dry cortical bone shavings are divided into 3 portions, preferably an exemplary division of 75% (dry cortical bone shavings—2), 17% (dry cortical bone shavings—1) and 8% all by volume. The division can vary within ranges 80-70%; 20-15%; and 15-5% with the understanding the powder should be no less than 5% and the cortical shavings no more than 80% in order for the composition to adequately perform. Only the 8% portion of the dry cortical bone shavings are ground to 106-300 um utilizing a bone grinder. The remaining portions are not ground and move to the next process. The dry morselized cancellous bone is ground to 1000-1700 um utilizing a bone grinder on slow setting. This is called "crushed cancellous".

Figure 11:
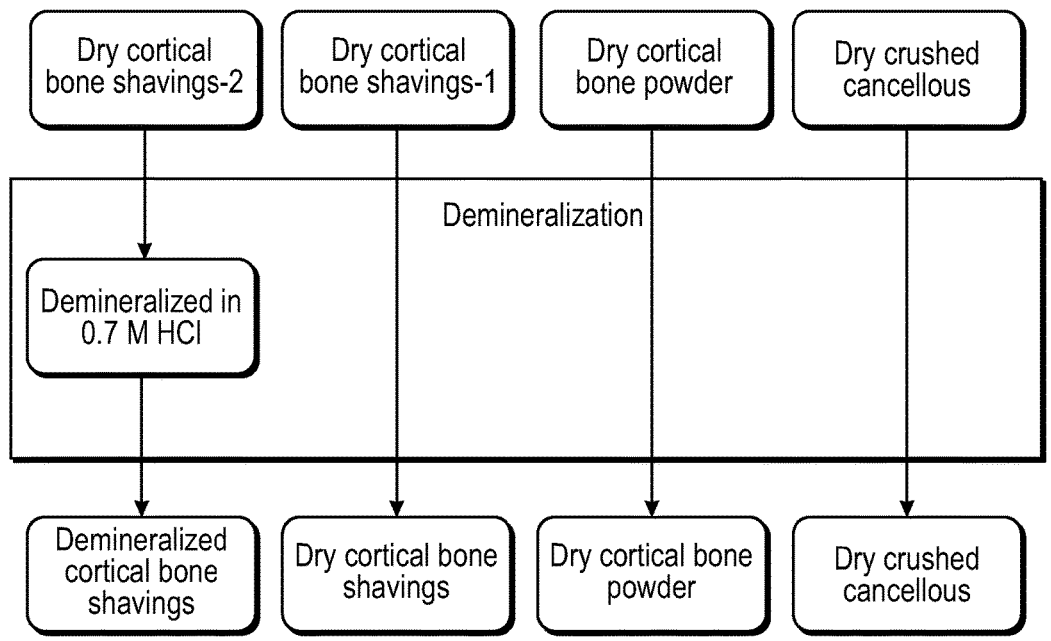
FIG. 11 shows the subprocess of demineralization taken from FIG. 7.

The Demineralizing subprocess is schematically shown in FIG. 11. The dry cortical bone shavings—2 is mixed with 0.7 HCL solution at a 20:1 ratio (20 ml of 0.7 HCL to 1 g of bone). The solution containing the tissue is placed on a magnetic stir plate for 59 minutes. It is understood the timing can vary based on the equipment and procedures used and the above is exemplary of the preferred process for the inventors' equipment. After decanting the liquid, the particulate tissue is mixed with sterile water at a 20:1 ratio (20 ml of sterile water to 1 g of bone). The solution containing the tissue is placed on a magnetic stir plate for 4 minutes. The process of decanting, mixing and incubating for 4 minutes is repeated with PBS solution. After decanting the PBS, the shavings are mixed with sterile water at a 20:1 ratio (20 ml of sterile water to 1 g of bone). The solution containing the tissue is placed on a magnetic stir plate for 9 minutes. The water waste solution is decanted and the demineralized shavings are stored at −80° C.

Figure 12:
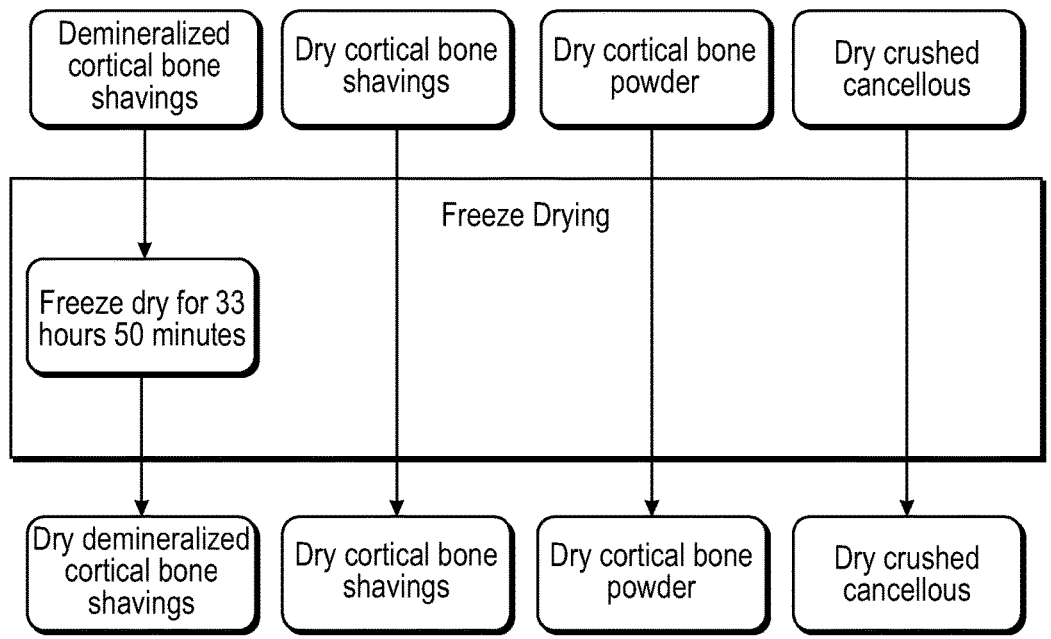
FIG. 12 shows the subprocess of freeze-drying taken from FIG. 7.

The second Freeze-Drying subprocess is shown in FIGS. 12 and 14. The demineralized cortical bone shavings are then prepared to undergo the freeze drying process again. The shavings are placed on separate sterile drying trays. The drying trays are then placed inside of a freeze dryer which is set to run for 33 hours 50 minutes. This cycle has shown to sufficiently dry the tissue without affecting the structural and chemical properties of the tissue.

Figure 13:
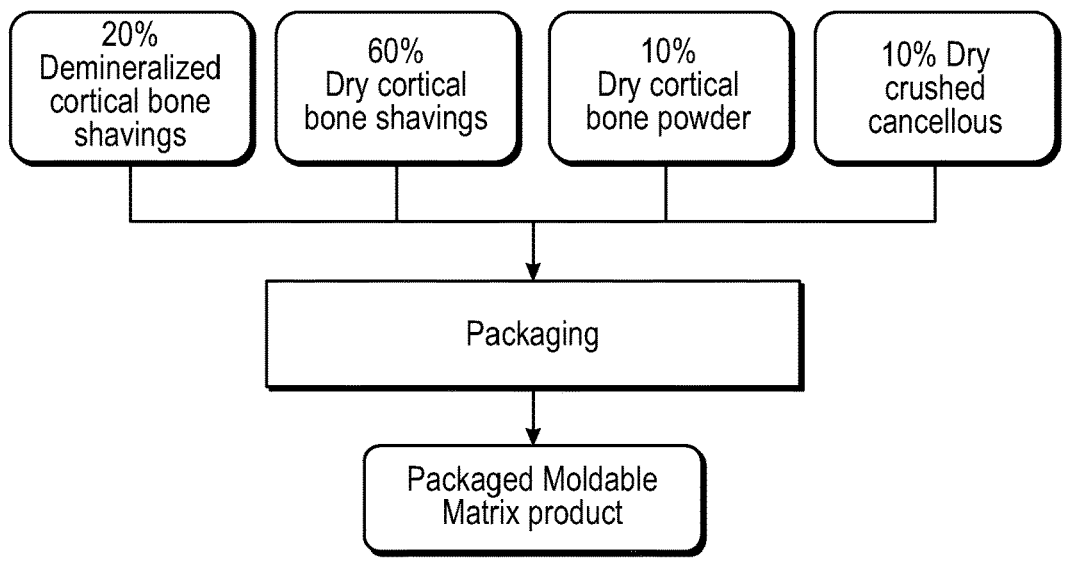
FIG. 13 shows the subprocess of packaging taken from FIG. 7.

The Packaging subprocess is shown in FIG. 13. Final processed mineralized and demineralized cortical shavings, crushed cancellous and cortical powder are combined at preferably an exemplary combination of 20% (0.2 g per 5 cc unit) dry demineralized cortical bone shavings, 60% dry mineralized cortical bone shavings, 10% dry cortical bone powder and 10% dry crushed cancellous and packaged in validated final packaging. The mixture is aseptically measured into jars; each jar closed tightly. The outer packaging used is a chevron type pouch allowing the end user to easily present the sterile inner pouch containing the product to a sterile field. The packaged final product is stored at room temperature or frozen until it is distributed to the end user. It is believed the above combination of the 4 constituent components is an optimum ratio. It is further understood variation of plus or minus 5% in and of the four materials is considered to be within the scope of the present invention such that the final product could have 25-15% dry demineralized cortical bone shavings; 65-55% dry mineralized cortical bone shavings; 15-5% dry cortical bone powder; and 15-5% dry crushed cancellous and are feasible to form the moldable bone composition 10.

The final product when used can be mixed with sterile water, lactated Ringer's solution, saline solution, normal saline, blood, plasma or other suitable liquid to achieve the moldable characteristics needed for the surgical repair of a bone malady. In a related co-pending application attorney docket number DN0257CIP, this mixture is combined with a fluid containing cells including stem cells.

Figure 3:
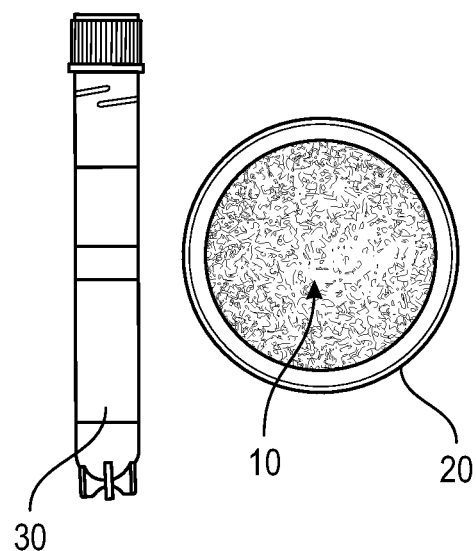
FIG. 3 is a photograph of the moldable bone composition in a container and the vial of cells removed from the sealed bag.
Figure 4:
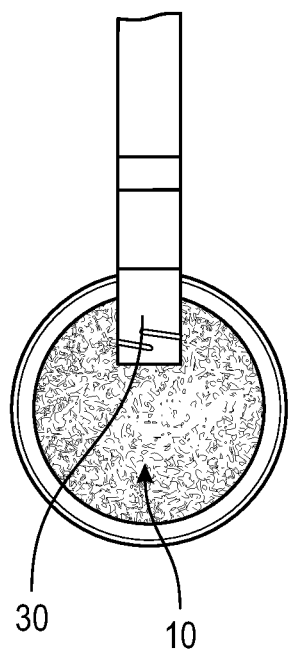
FIG. 4 is a photograph of the freeze-dried moldable bone composition in a container being wetted with the cells being added moistening the composition.
Figure 5:
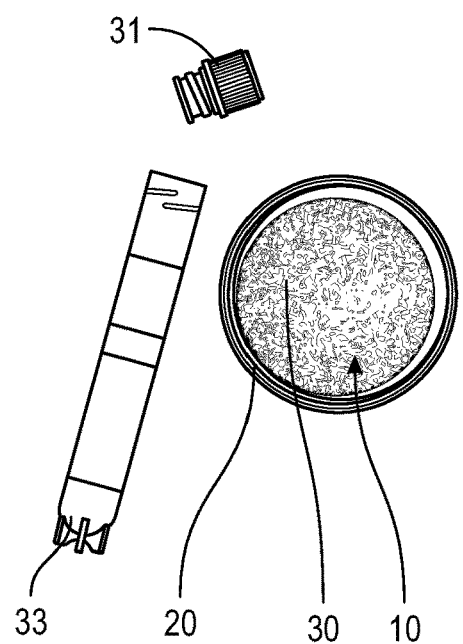
FIG. 5 is a photograph of the wetted moldable bone composition after the cells have been added.
Figure 6:
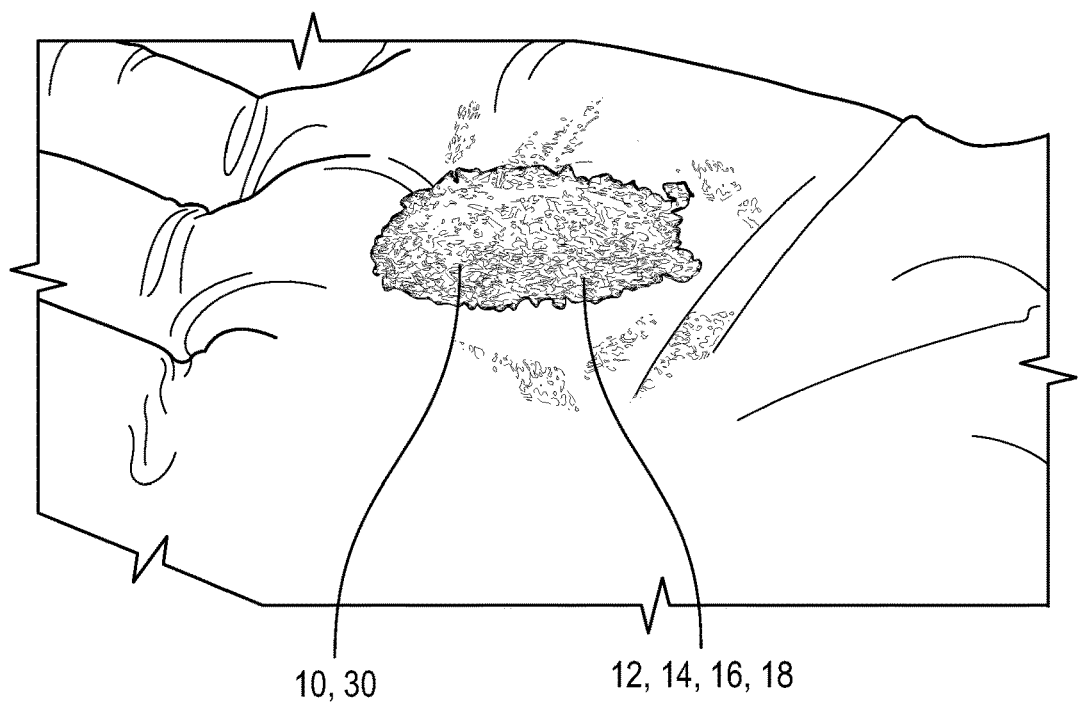
FIG. 6 is a photograph of the moldable bone composition after wetting and mixing.

With reference to FIGS. 1-6, photographs of the moldable bone composition are illustrated. With reference to FIG. 1, a finished moldable bone composition 10 is shown in a container 20 sealed in a plastic bag 50. The moldable bone composition 10 has four primary freeze-dried elements as illustrated, a demineralized cortical bone shaving portion 12, a mineralized cortical bone shaving portion 14, a powdered cortical bone portion 16 and crushed cancellous portion 18. These are divided in a particular ratio or proportion such that the moldable bone composition 10, when wetted, can have the osteogenic effect needed for bone repair when applied to a bone defect or bone void. With reference to FIG. 2, the freeze-dried composition 10 is shown in a package 50 that further includes a vial of cells 30 including stem cells. The cells 30 are suspended in a fluid in the vial 33. The components have a package insert 40 and are all sealed in packaging 50 as shown. With reference to FIG. 3, when the moldable composition 10 is taken from the package 50 and laid on a drape as illustrated, the container 20 has the freeze-dried elements in proper proportion as previously discussed. The vial 33 filled with a liquid laden with cells 30 is shown lying adjacent to the container 20 holding the composition 10. The physician can then take the vial 33, remove the cap 31 from the vial body 33 and pour the contents directly onto the freeze-dried composition 10 wetting the composition, as shown in FIG. 4. In FIG. 5, the empty vial 33 is shown next to the container 20 with the wetted moldable bone composition 10. With reference to FIG. 6, once the bone composition 10 has been wetted and mixed, the physician can withdraw the wetted composition from the container 20 and mold it into any desired shape he needs. This is particularly useful when packing a spinal fusion implant or a bone defect or any other component where an osteogenic beneficial enhancement of bone growth is to be encouraged. While in the illustrated embodiment, a vial 33 with fluid laden with cells 30 is shown as the fluid in which the composition 20 is wetted, it is understood that any number of appropriate fluids could be used when wetting the material such as sterile water, lactated Ringer's solution, normal saline, plasma, blood or any other commonly used material such that the freeze-dried composition becomes wetted and is able to be molded into the desired shape.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A moldable bone composition for treatment of osseous defects and bone voids consisting of a mixture of:
    cortical bone and cancellous bone, the cortical bone is formed in three portions, a dry mineralized shaving portion and a dry demineralized shaving portion and a dry mineralized powder portion; the cancellous bone is formed in a dry mineralized crushed cancellous portion, the portions are each dried by freeze-drying and mixed together to form a freeze-dried bone composition having four primary freeze-dried elements in a particular ratio or proportion forming the mixture, the freeze-dried bone composition packaged in a container with the mixture of the four primary freeze-dried elements dry configured to be molded to a desired shape by a physician after opening the package and wetting the composition with a suitable liquid to achieve moldable characteristics;
    a quantity of cells including stem cells suspended in a volume of suitable liquid or fluid in a vial for wetting the bone composition to form a wetted moldable bone composition configured to be molded into the desired shape for packing a spinal fusion implant or a bone defect or void; and
    wherein the freeze-dried bone composition in the container has the quantity of cells, including stem cells suspended in the liquid poured from the vial into the container to create the wetted bone composition with cells.

2. The moldable bone composition of claim 1 wherein the crushed cancellous bone is made from freeze-dried morselized cancellous ground to a size of 1000 to 1700 microns.

3. The moldable bone composition of claim 1 wherein the cortical bone powder is ground to 300 microns or less.

4. The moldable bone composition of claim 1 wherein the cortical shavings are long thin strips cut from cortical bone plates having a length of greater than 5 cm.

5. The moldable bone composition of claim 4 wherein the cortical shavings are strands having a length greater than 3 mm.

6. The moldable bone composition of claim 1 wherein the mixture has a percentage of demineralized cortical bone shaving portion by weight in the range of 15 to 25%.

7. The moldable bone composition of claim 1 wherein the mixture has a percentage of mineralized dry cortical bone shaving by volume in the range of 70 to 50%.

8. The moldable bone composition of claim 1 wherein the mixture has a percentage of mineralized dry cortical bone powder by volume in the range of 5 to 15%.

9. The moldable bone composition of claim 1 wherein the mixture has a percentage of dry crushed cancellous by volume in the range of 5 to 15%.

10. The moldable bone composition of claim 1 wherein the moldable bone composition has a percentage of demineralized cortical bone shaving by weight of 20%.

11. The moldable bone composition of claim 1 wherein the moldable bone composition has a percentage of dry mineralized cortical bone shaving by volume of 60%.

12. The moldable bone composition of claim 1 wherein the moldable bone composition has a percentage of dry cortical bone powder by volume of 10%.

13. The moldable bone composition of claim 1 wherein the moldable bone composition has a percentage of dry crushed cancellous by volume of 10%.

14. The moldable bone composition of claim 1 wherein the moldable bone composition has a percentage of 20% demineralized cortical bone shaving, 60% dry mineralized cortical bone shaving, 10% dry cortical bone powder and 10% dry crushed cancellous.

15. The moldable bone composition of claim 1 wherein the composition formed as a freeze-dried material packaged in jars wherein the packaged mixture is stored at room temperature or frozen.

* * * * *